(12) United States Patent
Vanmoor

(10) Patent No.: US 6,277,883 B1
(45) Date of Patent: Aug. 21, 2001

(54) METHOD OF TREATING MALE IMPOTENCE BY ENHANCING THE EFFECTIVENESS OF THE HUMAN IMMUNE SYSTEM

(76) Inventor: Arthur Vanmoor, 22 SE. 4 St., Boca Raton, FL (US) 33432-6016

( * ) Notice: Subject to any disclaimer, the term of this patent is extended or adjusted under 35 U.S.C. 154(b) by 0 days.

(21) Appl. No.: 09/717,634

(22) Filed: Nov. 21, 2000

(51) Int. Cl.$^7$ .......................... A61K 31/22; A61K 31/195
(52) U.S. Cl. ............................................. 514/550; 514/562
(58) Field of Search ..................................... 514/550, 562

(56) References Cited

U.S. PATENT DOCUMENTS

| | | | | |
|---|---|---|---|---|
| 5,626,831 | * | 5/1997 | Van Moerkerken | 424/9.2 |
| 5,707,967 | * | 1/1998 | Vanmoor | 514/19 |
| 5,708,029 | * | 1/1998 | Vanmoor | 514/562 |
| 5,767,157 | * | 6/1998 | Van Moerkerken | 514/562 |

\* cited by examiner

*Primary Examiner*—Raymond Henley, III
(74) *Attorney, Agent, or Firm*—Otto S. Kauder

(57) ABSTRACT

There is disclosed a method of treating male impotence in a person in need of such treatment, which comprises enhancing the effectiveness of the person's immune system by the administration to such person of at least one aliphatic sulfur compound, preferably a sulfur-containing amino-acid derivative having the formula (I)

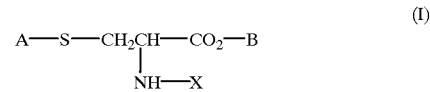

in which A is hydrogen or a carboxymethylene -CH$_2$CO$_2$H group, B is hydrogen or an alkyl group having 1 to 3 carbon atoms, and X is hydrogen, or an acyl group —CO—R in which R is an alkyl group having 1 to 3 carbon atoms, or a pharmaceutically acceptable salt of such compound.

23 Claims, No Drawings

METHOD OF TREATING MALE IMPOTENCE BY ENHANCING THE EFFECTIVENESS OF THE HUMAN IMMUNE SYSTEM

BACKGROUND OF THE INVENTION

1. Field of the Invention.

This invention relates to a method of treating a man suffering from an impotence condition with an agent that enhances the effectiveness of the human immune system to mitigate and where possible eliminate the impotence and enhance the man's stamina.

2. Description of Related Art.

The human immune system functions to maintain human individuality by fighting off foreign entities. The MERCK MANUAL, 16$^{th}$ edition, published 1992, at pages 279 to 303, which portion is here incorporated by reference, contains a detailed description of the parts of the immune system and of immunodeficiency diseases and hypersensitivity disorders to which it is subject. A table at pages 284–5 titled "Cytokines" lists the major effects of such cytokines or immunoeffective polypeptides as interleukin types, interferon types, alpha- and beta-tumor necrosis factor, three types of colony-stimulating factor, and alpha- and beta-transforming growth factor. A table at page 303 lists disorders with increased susceptibility to unusual infections. Nothing in this publication relates to an impotence condition or remedies therefor.

As is well known, remedies for male impotence and insufficient stamina have been sought for generations by a great variety of methods, and with the increasing application of science some successes have been achieved. However, the search for better remedies for this as well as other suffering conditions is enormously costly. For economic reasons, moreover, the search tends to be skewed in the direction of finding novel remedies proprietary to their discoverers and owners. Novel remedies, of course, come into being with nothing known about either their safety or their effectiveness, so that both of these essential attributes need to be exhaustively studied before they can be used as intended.

In contrast, the art has tended to neglect the exploration of therapeutic properties of known substances that humans have been safely ingesting for untold generations. Along these lines, the present inventor has been able to bring about in susceptible individuals within a limited and reproducible time the appearance of headache, elevated blood pressure, facial pimples, signs of the so-called common cold, and pains in a joint by administering selected foods, food ingredients, and relatively harmless household chemicals as trigger substances, and to use these as research tools to study the effectiveness of certain nutrient substances in relieving these artificially produced conditions as well as their natural counterparts. As a result, certain water soluble amino carboxylic acid compounds are disclosed in U.S. Pat. No. 5,707,967 as effective against facial pimples; certain water soluble amino carboxylic acid compounds are disclosed in U.S. Pat. No. 5,626,831 as effective against the common cold; certain water soluble amino carboxylic acid compounds are disclosed in U.S. Pat. No. 5,707,967 as effective against headache; certain water soluble amino carboxylic acid compounds are disclosed in U.S. Pat. No. 5,708,029 as effective against elevated blood pressure, and certain water soluble amino carboxylic acid compounds are disclosed in US patent no. 5,767,157 as effective against pain in a joint.

SUMMARY OF THE INVENTION

In accordance with this invention, there is provided a method of treating in a male person in need thereof an impotence condition, which comprises the administration to such person of at least one aliphatic sulfur compound. Administration of the aliphatic sulfur compound according to the invention is believed to enhance the effectiveness of the human immune system and thereby mitigate the impotence condition.

The aliphatic sulfur compound preferably includes a sulfur-methylene moiety such as—

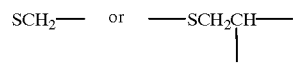

More preferably, the aliphatic sulfur compound also includes a carboxyl group, as in

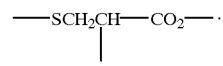

Still more preferably, the aliphatic sulfur compound is a sulfur-containing amino-acid derivative of an ethyl sulfide having the formula (I)

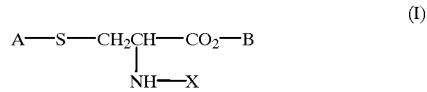

in which A is hydrogen or a carboxymethylene -CH$_2$CO2H group, B is hydrogen or an alkyl group having 1 to 3 carbon atoms, and X is hydrogen, or an acyl group —CO—R in which R is an alkyl group having 1 to 3 carbon atoms, or a pharmaceutically acceptable salt of such compound.

In this compound, the ethyl sulfide group

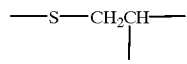

is believed to be responsible for the beneficial activity observed while the attached groups A, —NHM, and —CO$_2$B assist in delivering the compound to the site within the human organism where the beneficial activity is exerted.

In one preferred embodiment, A is hydrogen.

In a further preferred embodiment, A, B, and X are not simultaneously hydrogen. Particularly suitable illustrative derivatives having the formula given above are tabulated by showing the assignments of A, B, and X in the above formula:

| Compound | A | B | X |
|---|---|---|---|
| 1 | -CH$_2$CO$_2$H | H | H |
| 2 | H | H | COCH$_3$ |
| 3 | H | CH$_3$ | H.HCl |
| 4 | H | C$_2$H$_5$ | H.HCl |
| 5 | H | H | H |
| 6 | H | H | H.HCl |

The present invention is based on the recognition that enhancing the effectiveness of the immune system in a person can be beneficial in augmenting the person's innate ability to resist the initiation and intensification of an impotence condition. Consequently, the quality of life is improved.

In increasing the effectiveness of the human immune system according to this invention, mega-nutrient doses of 2 to 20 grams of a compound or compounds of formula (I) can be administered to a male after signs of decline in stamina appear in order to diminish its extent and duration. Doses can be administered in any convenient manner, as by oral administration in any of the usual dosage forms, such as tablets, capsules, solutions, and dispersions in liquid foods such as soups and fruit juices. Alternatively, there can be given sterile solutions by direct injection into the bloodstream of the person to be treated, as well as by rectal suppositories.

EXAMPLE 1

A 52 year old man with difficulties in maintaining erection and with limited success with the Viagra® brand remedy for impotence was given forty grams of composition comprising several compounds of formula (I) daily spread over the meals of each day and after four weeks of this treatment was achieving normal results, that is results comparable to those the same man achieved at age 30.

What is claimed is:

1. A method of treating a male impotence condition in a person in need of such treatment, which comprises the administration to such person of at least one aliphatic sulfur compound.

2. The method of claim 1, in which the aliphatic sulfur compound includes at least one of the moieties

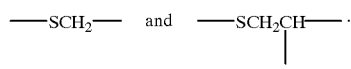

3. The method of claim 1, in which the aliphatic sulfur compound includes a carboxyalkylene group

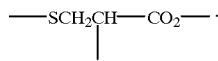

4. The method of claim 1, in which the aliphatic sulfur compound is an ethyl sulfide compound including the active group

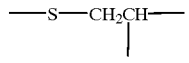

and attached thereto one group linked to sulfur and two groups linked to carbon, said groups assisting in delivering said ethyl sulfide compound to the site where the beneficial activity is exerted.

5. The method of claim 4, in which the group linked to sulfur is A, wherein A is hydrogen or a carboxymethylene group —$CH_2CO_2H$.

6. The method of claim 4, in which a group linked to carbon is B, wherein B is H or an alkyl group having 1 to 3 carbon atoms.

7. The method of claim 4, in which a group linked to carbon is —NHX wherein X is hydrogen or an acyl group —CO—R, R being an alkyl group having 1 to 3 carbon atoms.

8. The method of claim 4, in which the ethyl sulfide compound is a sulfur-containing amino-acid derivative having the formula (I)

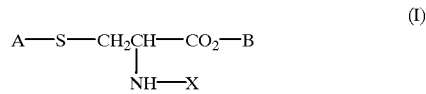

in which A is hydrogen or a carboxymethylene -$CH_2CO_2H$ group, B is hydrogen or an alkyl group having 1 to 3 carbon atoms, and X is hydrogen, or an acyl group —O—R in which R is an alkyl group having 1 to 3 carbon atoms, or a pharmaceutically acceptable salt of such compound.

9. The method of claim 8, wherein said amino-acid derivative is administered orally with food.

10. The method of claim 8, wherein said amino-acid derivative is administered by injection into the bloodstream.

11. The method of claim 8, wherein said amino-acid derivative is administered by rectal suppository.

12. The method of claim 8, wherein said amino-acid derivative is administered in one to eight daily doses of 2 to 20 grams each.

13. The method of claim 8, wherein the total of said amino-acid derivative administered daily is in the range of 10 to 50 grams.

14. The method of claim 8, wherein said amino-acid derivative is the compound of formula (I) in which A is —$CH_2CO_2H$, B is H, and X is H.

15. The method of claim 8, wherein said amino-acid derivative is the compound of formula (I) in which A is H, B is H, and X is $COCH_3$.

16. The method of claim 8, wherein said amino-acid derivative is the compound of formula (I) in which A is H, B is $CH_3$, and X is HHC1.

17. The method of claim 8, wherein said amino-acid derivative is the compound of formula (I) in which A is H, B is H, B, $C_2H_5$ and X is HHC1.

18. The method of claim 8, wherein said amino-acid derivative is the compound of formula (I) in which A is H, B is H, and X is H.

19. The method of claim 8 wherein said amino-acid derivative is the compound of formula (I) in which A is H, B is H, and X is HHC1.

20. The method of claim 8, wherein said person experiences relief from the effects of male impotence.

21. The method of claim 8 wherein after treatment male impotence is not observed.

22. A method of treating a male impotence condition in a person in need of such treatment, which comprises enhancing the effectiveness of the person's immune system by the administration to such person of at least one aliphatic sulfur compound.

23. The method of claim 22, wherein the aliphatic sulfur compound is at least one sulfur-containing amino-acid derivative having the formula (I)

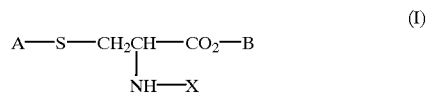

in which A is hydrogen or a carboxymethylene -$CH_2CO2H$ group, B is hydrogen or an alkyl group having 1 to 3 carbon atoms, and X is hydrogen, or an acyl group —CO—R in which R is an alkyl group having 1 to 3 carbon atoms, or a pharmaceutically acceptable salt of such compound.

* * * * *